United States Patent
Hall et al.

(10) Patent No.: US 7,842,506 B2
(45) Date of Patent: Nov. 30, 2010

(54) APOLIPOPROTEIN E GENOTYPING AND ACCOMPANYING INTERNET-BASED HEALTH MANAGEMENT SYSTEM

(75) Inventors: Christopher Hall, San Francisco, CA (US); Vance Lanier, Jr., Atlanta, GA (US); David T. Shewmake, San Franscisco, CA (US)

(73) Assignee: Berkeley Heartlab, Inc., Alameda, CA (US)

( * ) Notice: Subject to any disclaimer, the term of this patent is extended or adjusted under 35 U.S.C. 154(b) by 638 days.

(21) Appl. No.: 11/702,961

(22) Filed: Feb. 6, 2007

(65) Prior Publication Data

US 2007/0224619 A1  Sep. 27, 2007

Related U.S. Application Data

(63) Continuation-in-part of application No. 10/854,402, filed on May 26, 2004, now Pat. No. 7,226,792.

(60) Provisional application No. 60/771,138, filed on Feb. 6, 2006, provisional application No. 60/473,715, filed on May 27, 2003.

(51) Int. Cl.
*G01N 33/92* (2006.01)

(52) U.S. Cl. ............ 436/71; 436/63; 436/86; 705/3

(58) Field of Classification Search ........ 436/63, 436/71, 86; 435/6, 11; 422/68.1, 99; 702/19, 702/20, 32; 705/2, 3; 600/300
See application file for complete search history.

(56) References Cited

U.S. PATENT DOCUMENTS

| | | | |
|---|---|---|---|
| 6,171,237 B1 * | 1/2001 | Avitall et al. | 600/300 |
| 6,589,169 B1 * | 7/2003 | Surwit et al. | 600/300 |
| 2002/0019586 A1 * | 2/2002 | Teller et al. | 600/300 |
| 2003/0208108 A1 * | 11/2003 | Shewmake et al. | 600/300 |
| 2005/0010087 A1 * | 1/2005 | Banet et al. | 600/300 |
| 2007/0068539 A1 * | 3/2007 | Hall et al. | 128/898 |
| 2007/0071643 A1 * | 3/2007 | Hall et al. | 422/62 |
| 2008/0050740 A1 * | 2/2008 | Cassidy | 435/6 |

* cited by examiner

*Primary Examiner*—Maureen M Wallenhorst

(57) ABSTRACT

The invention provides a system for monitoring a patient that includes: 1) a blood test that measures an Apo E genotype or a derivative thereof from the patient to generate Apo B information; 2) a database that receives and stores the patient's Apo E information; and 3) an Internet-based system connected to the database and configured to process the Apo E information with an algorithm that, in response, generates a diet and treatment plan for the patient.

4 Claims, 4 Drawing Sheets

| | | Apo E2 | | Apo E3 | | Apo E4 | |
|---|---|---|---|---|---|---|---|
| 40 | Genotype | 2/2 | 2/3 | 3/3 | 2/4 | 3/4 | 4/4 |
| 41 | Population Frequency | (1%) | (10%) | (62%) | (2%) | (20%) | (5%) |
| 42 | CVD Risk Assessment | Intermediate | | Lowest | | Highest (42% increased risk of CVD) | |
| 43 | Recommended Diet Type | Preventative (25%) or Moderate (35%) fat diet | | Preventative (25%) or Moderate (35%) fat diet | | Very low fat (20%) | |
| 44 | Affect of Low Fat Diet | ↓LDL (minimal) ↑small dense LDL | | ↓LDL ↑small dense LDL | | ↓LDL (significant) ↓small dense LDL | |
| | Affect of Moderate Fat Diet | No known effect | | ↓LDL ↓small dense LDL | | ↓LDL ↑small dense LDL | |

Patient Blood Test

*June 23, 2005*

Legend: ☐ below goal  ▨ above goal, below alert  ▨ above alert

Key Risk Factors

Cholesterol and Apo E Blood Tests

| Test Type | 9 / 2004 | 12 / 2004 | 3 / 2005 | BHL Goal |
|---|---|---|---|---|
| LDL IIIa+IIIb | | | 18 | 16 |
| HDL IIa | | 58 | | 50 |
| LDL-C | 130 | | | 120 |
| Apo E | | 2/2 | | |

▸ View Recommended Diet Plan

Additional Blood Tests

| Test Type | 9 / 2004 | 12 / 2004 | 3 / 2005 | BHL Goal |
|---|---|---|---|---|
| Total Cholest. | | | 18 | 16 |
| Triglycerides | | 18 | | 50 |
| Insulin | | | 18 | 16 |
| Fibrinogen | | 58 | 62 | 50 |
| Apoprotein | | 127 | 123 | 120 |
| Lipoprotein | | 21 | | 16 |
| Triglycerides | 51 | | 42 | 50 |
| Homocysteine | 130 | | 123 | 120 |

Fig. 4

APOLIPOPROTEIN E GENOTYPING AND ACCOMPANYING INTERNET-BASED HEALTH MANAGEMENT SYSTEM

This application is a continuation-in-part of U.S. patent application Ser. No. 10/854,402, filed May 26, 2004, now U.S. Pat. No. 7,226,792 issued Jun. 5, 2007, which claims the benefit of U.S. Provisional Application Ser. No. 60/473,715, filed May 27, 2003. This application also claims the benefit of U.S. Provisional Application Ser. No. 60/771,138, filed on Feb. 6, 2006.

STATEMENT REGARDING FEDERALLY SPONSORED RESEARCH OR DEVELOPMENT

Not Applicable

BACKGROUND

1. Field of the Invention

The present invention relates to a patient-monitoring system that processes information from one or more blood tests, e.g. a blood test that measures the Apo E genotype.

2. Description of the Related Art

Although mortality rates for cardiovascular disease (CVD) have been declining in recent years, this condition remains the primary cause of death and disability in the United States for both men and women. In total, more than 60 million Americans have a form of CVD, which includes high blood pressure (approximately 50 million Americans), coronary heart disease (12.5 million), myocardial infarction (7.3 million), angina pectoris (6.4 million), stroke (4.5 million), congenital cardiovascular defects (1 million), and congestive heart failure (4.7 million). Atherosclerotic cardiovascular disease (AS-CVD), a form of CVD, can cause hardening and narrowing of the arteries, which in turn restricts blood flow and impedes delivery of vital oxygen and nutrients to the heart. Progressive atherosclerosis can lead to coronary artery, cerebral vascular, and peripheral vascular disease which in combination result in approximately 75% of all deaths attributed to CVD.

Various lipoprotein abnormalities, including elevated concentrations of low-density lipoprotein cholesterol (LDL cholesterol), increased small dense LDL cholesterol subfractions and others, are causally related to the onset of ASCVD because over time these compounds contribute to a harmful formation and build up of atherosclerotic plaque in an artery's inner walls, thereby restricting blood flow. The likelihood that a patient will develop ASCVD generally increases with increased levels of LDL cholesterol, which is often referred to as 'bad cholesterol'. Conversely, high-density lipoprotein cholesterol (HDL cholesterol) can function as a 'cholesterol scavenger' that binds LDL cholesterol and transports it back to the liver for re-circulation or disposal. This process is called 'reverse cholesterol transport'. A high level of HDL cholesterol is therefore associated with a lower risk of developing heart disease and stroke, and thus HDL cholesterol is typically referred to as 'good cholesterol'.

Apolipoprotein E (Apo E) plays an important role in lipoprotein metabolism, functioning as a ligand for lipoprotein receptors. It is one of the most common genes affecting LDL cholesterol levels and is linked to CVD, heart disease, type II Alzheimer's disease, and hypercholesterolemia type III. Different Apo E isoforms alter plasma lipoprotein concentrations having different receptor affinities. This is often phenotypically expressed in combination with varying environmental stimuli or genetic associations. The human Apo E gene has three common alleles (e2, e3, e4) coding for the Apo E protein as three isoforms (E2, E3, E4), which vary in the amino acids present at positions 112 and 158 of the protein. There are three homozygous (e4/e4, e3/e3, and e2/e2) and three heterozygous (e4/e3, e4/e2, and e3/e2) genotypes and phenotypes resulting from simple co-dominant Mendelian inheritance of the Apo E gene. The Apo E genotypes include Apo E2 (e2/e2, e2/e3), Apo E3 (e3/e3, e2/e4), and Apo E4 (e3/e4, e4/e4). Isoforms of the Apo E protein are created primarily in the liver and brain, and transport lipids to help clear dietary fats, such as triglycerides, from the blood.

Mechanistically, Apo E2 is associated with a slow conversion of intermediate density lipoprotein cholesterol (IDL cholesterol) to LDL cholesterol, leading to a decrease in plasma cholesterol and increased triglycerides. Apo E3 has normal lipid metabolism, thus no genotype impact. Apo E4 is associated with an inhibition of the normal cholesterol clearing process, which implies a limitation of HDL cholesterol binding leading to an increase in LDL cholesterol and triglycerides.

Recent studies indicate that patients with the genotype of at least one Apo E e4 allele (e4/4 and e4/3; 25% of population) have the highest for CVD and are associated with various clinical atherosclerotic syndromes. The Apo E e4 allele is therefore a 'genetic marker' for these conditions. However, genetic and environmental stress factors must contribute to the phenotypic expression of associated heart disease. For example, patients with the Apo E e4 allele have a predisposition to elevated cholesterol and increased cardiac risk when their diet is high in saturated fats and/or alcohol. Environmental factors, such as diet and exercise, may therefore dictate whether or not a patient actually develops these harmful conditions.

Patients with the late onset of type II Alzheimer's disease, which typically develops after age 65, have also been linked to the Apo E e4 genotype. The risk of developing this condition is increased in a patient homozygous for e4 (i.e., e4/e4) compared to a heterozygous patient (i.e., e2/e4 or e3/e4). About 35 to 50% of all patients with late-onset Alzheimer's express this gene.

Patients with the Apo E2 genotype (about 10% of the population) typically have a slower conversion metabolism, leading to a decrease in plasma cholesterol and increased triglycerides. Studies show that patients with an Apo E e2/e2 combination (less than 1% of the population) have a predisposition to Type III Hyperlipidemia, which may account for as much as 5% of all cases of early coronary heart disease (CHD). This means that patients with this marker are genetically predisposed to increased CVD risk.

A blood test, called Apo E genotype, can identify a given patient's isoform variation (genotype). This blood test can be coupled with blood tests for various other cardiac risk markers, including a lipoprotein analysis (also called a lipoprotein profile or lipid panel) that measures, among other compounds, blood levels of total cholesterol, LDL cholesterol, and HDL cholesterol. One method for measuring HDL and LDL cholesterol is described in U.S. Pat. No. 6,812,033, entitled 'Method for identifying risk cardiovascular disease patients'. This patent, assigned to Berkeley HeartLab Inc. and incorporated herein by reference, describes a blood test based on a gradient-gel electrophoresis (GGE). Gradient gels used in GGE are typically prepared with varying concentrations of acrylamide and can separate macromolecules with relatively high resolution compared to conventional electrophoretic gels. Sub-classes of both HDL and LDL cholesterol can be determined by GGE. For example, GGE can differentiate up to seven subclasses of LDL cholesterol (classified as LDL I, IIa, IIb, IIIa, IIIb, IVa, and IVb), and up to five subclasses of HDL (classified as HDL 2b, 2a, 3a, 3b, 3c). These tests correlate to a technique called analytic ultracentrifugation (AnUC), which is an established clinical research standard for lipoprotein subfractionation.

GGE can differentiate the most atherogenic particles, LDL IIIa, IIIb, and IVb, and also the most helpful HDL particle, HDL 2b. Elevated levels of LDL IVb, which represents the smallest LDL cholesterol particles, have been reported to have an independent association with arteriographic progression; a combined distribution of LDL IIIa and LDL IIIb typically reflects the severity of this trait. High levels of HDL 2b increase the efficacy of reverse cholesterol transport; while low levels of HDL 2b, indicating less efficient reverse cholesterol transport, can increase the risk of CVD and atherosclerosis.

SUMMARY OF THE INVENTION

In one aspect, the invention provides a system for monitoring a patient that includes: 1) a blood test that identifies the Apo E genotype, or a derivative thereof, from the patient to generate Apo E information; 2) a database that receives and stores the patient's Apo E information; and 3) an Internet-based system connected to the database and configured to process the Apo E information with an algorithm that, when combined with a panel of CVD-related blood tests and risk markers, generates diet treatment plans for the patient.

In one embodiment, the algorithm processes the Apo E information (e.g. an Apo E genotype) to generate a range of diet plans varying in percentages of recommended fat calories (i.e. the number of calories within the diet that come directly from fat). In other embodiments, the system also employs one or more blood tests that measure a distribution (i.e. subclasses) of cholesterol and/or cardiac risk markers, and in response, processes this and the Apo E information to generate diet treatment plans for the patient.

In embodiments, the system can include a messaging system configured to send a message describing the Apo E information or a corresponding diet plan to the patient's email address, wireless device, or monitoring device. The message, which can describe the patient's treatment plan, is typically a text message, SMS message, HTML-based message, or other form of message that propagates over an http, https, or wireless protocol. The messages can include a variety of content, including diet and exercise recommendations, recipes, program goals, progress toward goals, articles, educational content, links to web pages, or related content.

In other embodiments, the messaging system is additionally configured to receive messages from the patient. For example, the messaging system can send a message that includes a text field wherein the patient can enter a response. In this case, the Internet-based system typically includes a software component that parses the response entered in the text field once the message is received.

In a particular embodiment, the system measures blood test information measured from a GGE-based blood test, taken alone or combined with other blood tests. Such tests are described in U.S. Pat. No. 5,925,229, entitled "Low density lipoprotein fraction assay for cardiac disease risk", the contents of which are incorporated herein by reference.

The Internet-based system typically features a website with one or more web pages that display the Apo E information, taken alone or combined with other information. In embodiments, the website includes a first web interface that displays information for a single patient, and a second web interface that displays information for a group of patients. For example, a medical professional (e.g. a physician, nurse, nurse practitioner, dietician, or clinical educator) associated with a group of patients could use the second web interface to analyze the patient's Apo E information, and in response recommend a diet and exercise program. Both web interfaces typically include multiple web pages that, in turn, feature both static and dynamic content, described in detail below.

The system can also include a monitoring device that measures: 1) heart rate; 2) systolic, diastolic, and pulse blood pressure; 3) pulse oximetry; and 4) cardiac 'waveforms' that can be further processed to determine arrhythmias, blood pressure load, cardiac stroke volume, and other cardiac properties. The monitor can also connect to one or more external medical devices (e.g. a glucometer, gas analyzer) to measure other properties (e.g., blood glucose, $CO_2$) that the system can process along with the above-mentioned information. These properties can be measured daily as a one-time measurement, or quasi-continuously (e.g., every 30 seconds) during exercise. Preferably the monitoring device measures blood pressure without using a cuff in a matter of seconds, as described in detail below. This means patients can quickly and easily monitor blood pressure and other vital signs with minimal discomfort. With this device patients can easily measure their vital signs throughout the day (e.g., while at work), thereby generating a complete set of information, rather than just a single, isolated measurement. In addition, the monitoring device can collect weight and percent body fat from a bathroom scale (using, e.g., a wired or wireless link), and exercise-related properties, such as steps (using an internal pedometer circuit), calories burned (using sensor inputs and associated algorithms), and exercise time (using a simple clock).

In other embodiments, the monitoring device includes an interface (e.g., an RS232-based serial port, USB serial port, or wireless interface) to a personal computer. The wireless interface can include protocols such as Bluetooth™, 802.11, 802.15.4, and part-15. Typically, in this embodiment, the Internet-based system includes a software program that, when launched, collects vital sim and exercise information from the monitoring device. The Internet-based system may also link to 'chat rooms' or internal email systems that allow patients to communicate with one another.

'Apo E information', as used herein, means information collected from one or more blood tests that describe any property relating to Apo E, e.g. the Apo E gene, its alleles, and any lipoprotein that results from these components. 'Blood test information', as used herein, means information collected from one or more blood tests, such as a GGE test, lipid panel, or any conventional blood test. Blood test information can include concentration, density, amounts, or any other information describing blood-borne compounds, including but not limited to total cholesterol, LDL cholesterol (and subclass distribution), HDL cholesterol (and subclass distribution), triglycerides, Apo B particle, Apo B ultra particle, lipoprotein, Apo E genotype, fibrinogen, folate, $HbA_{1c}$, C-reactive protein, homocysteine, glucose, insulin, chlamydia, and other compounds. 'Vital sign information', as used herein, means information collected from patient using a medical device that monitors the patient. This information includes but is not limited to heart rate (measured at rest and during exercise), blood pressure (systolic, diastolic, and pulse pressure), blood pressure waveform, pulse oximetry, optical plethysmograph, electrical impedance plethysmograph, stroke volume, ECG and EKG, temperature, weight, percent body fat, and other properties. 'Exercise information', as used herein, means information that characterizes a patient's exercise habits, including but not limited to steps, miles run or biked, duration of any type of exercise, degree of exertion during exercise, calories burned during exercise, and heart rate and other cardiovascular information measured during exercise. 'Personal information', as used herein, means information such as age, gender, medical history, ethnicity, current medications, and other information that can be used alone or in combination with the above-mentioned properties to, among other things, develop metabolic and cardiovascular risk profiles to diagnose and manage a patient.

The invention has many advantages, particularly because it provides an Internet-based system that processes blood test information describing Apo E and other information to generate personalized diet and treatment plans for a patient. The Internet-based system also processes other information, such as vital sign information, and provides a mechanism that helps a patient comply with a personalized cardiovascular risk reduction program. Patient-specific programs can be quickly updated and modified. For example, after running an algorithm, the Internet-based system can provide content (e.g., recipes associated with a low-fat diet plan; detailed exercise programs) through both a website and messaging platform that sends information to the patient's email address, wireless device, or monitoring device. Ultimately the Internet-based system, monitoring device, and messaging platform combine to form an interconnected, easy-to-use tool that can engage the patient in a disease-management program, encourage follow-on medical appointments, and build patient compliance. These factors, in turn, can help the patient lower their risk for certain medical conditions, such as CHD and CVD.

These and other advantages of the invention will be apparent from the following detailed description and from the claims.

DETAILED DESCRIPTION OF THE INVENTION

Figure 1:
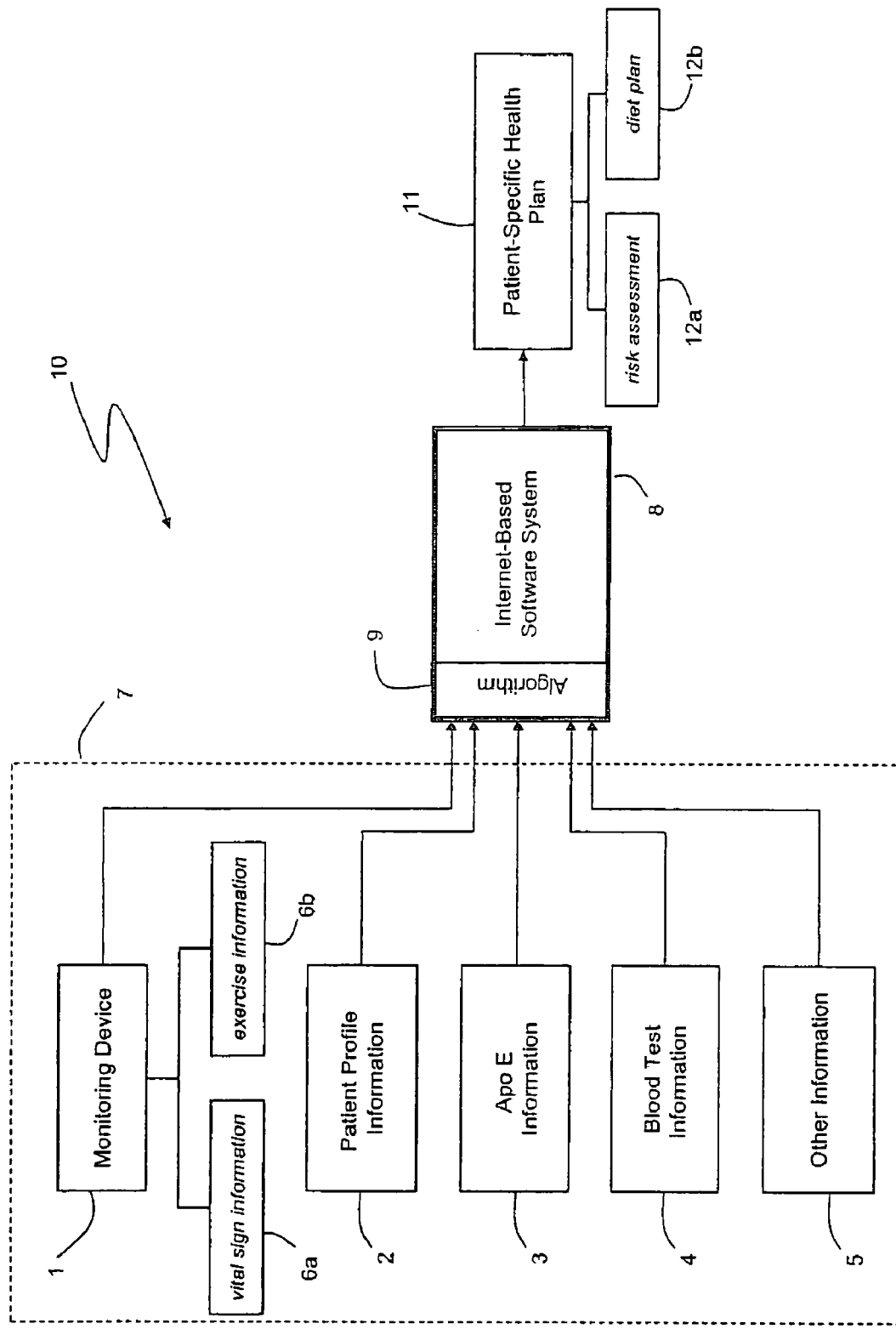
FIG. 1 is a schematic drawing of an Internet-based health management system that generates a patient-specific health plan by processing, e.g., Apo E information, blood test information, patient information, and information from a monitoring device.

FIG. 1 shows a schematic view of a health management system 10 featuring an Internet-based software system 8 that processes an array of inputs 7, particularly Apo E information 3 from an Apo E genotyping test. After processing the inputs 7, an algorithm 9 within the Internet-based software system 8 generates a patient-specific health plan 11 that features a risk assessment 12a that analyzes the patient's risk for CVD and related conditions, and a diet plan 12b engineered to ameliorate these conditions. Along with information from the Apo E genotyping test 3, the algorithm 9 typically accepts vital sign 6a and exercise 6b information from a monitoring device 1, patient profile information 2, blood test information 4, and other information 5 such as the patient's medications and medical history. The algorithm generates the risk assessment 12a, typically summarized as 'high', 'intermediate', and 'low', which can also include content, e.g. a detailed medical opinion or reference articles, describing the patient's condition. The diet plan 12b typically recommends an amount of fat within the patient's diet, e.g. patients with the Apo E2 genotype may benefit from a somewhat higher, healthy fat diet, while patients with the Apo E4 genotype may benefit from a low-fat diet.

The Apo E test used in the health management system is typically a conventional genetic test that involves DNA analysis by polymerase chain reaction (PCR) with restriction enzyme cleavage. Such a test is typically >99% accurate, takes a few hours to perform, and typically requires about 5 ml of whole blood from the patient.

Accompanying the Apo E test may be one or more additional blood tests that generate blood test information 4 that can help assess cardiac risk. For example, the blood may be a GGE-based blood test that detects blood-borne properties such as total cholesterol, LDL cholesterol, and HDL cholesterol, and sub-classes of LDL and HDL cholesterol. GGE typically differentiates up to seven subclasses of LDL cholesterol (classified as LDL I, IIa, IIb, IIIa, IIIb, IVa, and IVb), and up to five subclasses of HDL (classified as HDL 2b, 2a, 3a, 3b, 3c). Other complementary blood tests can detect blood test information 9 such as triglycerides, Apo B-Particle, Apo B ultra particle, lipoprotein, fibrinogen, folate, $HbA_{1c}$, C-reactive protein, homocysteine, glucose, insulin, and chlamydia.

Figure 2:
FIG. 2 shows a table used by an algorithm in the health management system of FIG. 1 that generates information describing patient-specific diet and risk factors based on three different genotypes of Apo E.

FIG. 2 shows a table 30 used by the algorithm described in FIG. 1 to generate the patient-specific diet plan. The table 30 shows different genotypes 40 corresponding to Apo E2, E3, and E4, along with the domestic populations 41 and a CVD risk assessment 42 that correspond to each genotype 40. Specifically, the table 30 shows that a patient's risk of developing CD is lowest for genotype E3, intermediate for genotype E2, and highest for genotype E4. Corresponding to this risk assessment 42 is a recommended diet 43, and the affect 44 both a low-fat diet and moderate-fat diet would have on the patient's total LDL cholesterol and small, dense LDL cholesterol. For example, the table 30 describes how patients with genotype E4 have the highest risk for CVD, likely resulting from a genetic metabolic lipid conversion response increasing "bad cholesterol", and therefore should follow a very low fat diet (fat content of approximately 20% of all calories). In most cases, this diet significantly lowers the patient's total LDL and small, dense LDL cholesterol in the absence of other negative environmental stimuli. For this patient population, a moderately low-fat diet typically lowers the patient's total LDL cholesterol, but not by the same degree as the low-fat diet. In this case, a commensurate reduction in the patient's HDL cholesterol reduces the extent of reverse cholesterol transport, thereby causing the patient's small, dense cholesterol to typically increase.

Patients of genotype Apo E3 have the lowest risk of CVD, and thus the table 30 recommends a preventative (fat content of approximately 25% of all calories) or moderate (fat content of approximately 35% of all calories) diet. Due to different metabolic lipid conversion, patients with this genotype that follow a low-fat diet typically see their LDL cholesterol decrease, while a moderate-fat diet lowers both LDL cholesterol and small, dense LDL cholesterol for these patients. The table 30 recommends that patients of genotype Apo E2 also follow a preventative or moderate fat diet. In this case, a low-fat diet typically lowers the patient's LDL cholesterol by a minimal amount, but also slightly increases their small, dense LDL cholesterol. A moderate-fat diet has no known lipid conversion affect on patients having this genotype.

Referring again to FIG. 1, the algorithm 9 operating on the Internet-based software system 8 can process Apo E information 3 and other blood test information 4, taken independently or in combination, to generate a corresponding diet plan 12b. The Examples below show three different diet plans corresponding to low-fat, moderate-fat, and preventative diets. Each Example includes: 1) a 'primary criteria', based on the patient's Apo E genotype, that the algorithm uses to select a particular diet plan; 2) a 'secondary criteria', based on blood test information other than the patient's Apo E information, that the algorithm can also use to select a particular diet plan; and 3) a table that shows a range of diet plans that depend on the number of daily calories recommended for a particular patient. The number of daily calories, and the associated diet plan, depends on a variety of factors, including the patient's age, sex, weight, medical history, Apo E information, and blood test information. Note that other diet plans can be associated with the Apo E information, and may therefore be used.

EXAMPLE 1

Moderate Fat Diet (35% of Total Calories are Fat Calories)

Primary Criteria
Apo E3 Genotype (lowest risk)
Secondary Criteria
a) HDL 2(b) ≦10% of HDL cholesterol (male); ≦20% (female)
b) Triglycerides 150-199 (mg/dL)
c) LDL IIIa+IIIb ≧35% of LDL-C cholesterol
d) Glucose ≧110 (mg/dL)
e) Insulin ≧12 (μU/ml)
f) Diabetes Mellitus
Recommended Diet Plan

| Food | 1200 cals. | 1600 cals. | 1800 cals. | 2000 cals. | 2400 cals. | 2800 cals. | 3000 cals. | 3600 cals. |
|---|---|---|---|---|---|---|---|---|
| Grain/Starch | 5 | 6 | 6 | 7 | 8 | 10 | 13 | 13 |
| Vegetable | 4 | 4 | 4 | 5 | 5 | 5 | 6 | 7 |
| Fruit | 2 | 4 | 4 | 4 | 5 | 5 | 6 | 8 |
| Dairy | 1 | 2 | 2 | 2 | 2 | 3 | 2 | 3 |
| Protein | 3 | 4 | 5 | 5 | 6 | 7 | 8 | 9 |
| Fat | 8 | 10 | 11 | 13 | 15 | 17 | 18 | 21 |
| Sweets/Alcohol | 0 | 0 | 1 | 2 | 3 | 3 | 3 | 4 |

Note
values in columns refer to points; see Appendix A for a description of corresponding foods

EXAMPLE 2

Preventative Diet (25% of Total Calories Are Fat Calories)

Primary Criteria
APO E2 genotype (intermediate risk)
Secondary Criteria
a) LDL IIIa+IIIb 16-34% of LDL-C cholesterol
b) LDL-C 100-159 (mg/dL)
c) Lp(a) ≧20 (mg/dL)
d) Homocysteine ≧14 (μmol/l)
e) APO B ≧110 (mg/dL)
Recommended Diet Plan

| Food | 1200 cals. | 1600 cals. | 1800 cals. | 2000 cals. | 2400 cals. | 2800 cals. | 3000 cals. | 3600 cals. |
|---|---|---|---|---|---|---|---|---|
| Grain/Starch | 5 | 6 | 7 | 8 | 11 | 12 | 13 | 16 |
| Vegetable | 4 | 4 | 4 | 5 | 5 | 5 | 7 | 7 |
| Fruit | 3 | 4 | 4 | 4 | 4 | 5 | 5 | 6 |
| Dairy | 2 | 2 | 3 | 3 | 3 | 3 | 3 | 4 |
| Protein | 4 | 6 | 6 | 6 | 8 | 10 | 11 | 14 |
| Fat | 5 | 5 | 7 | 8 | 9 | 11 | 12 | 13 |
| Sweets/Alcohol | 0 | 2 | 2 | 2 | 3 | 5 | 5 | 5 |

Note
values in columns refer to points; see Appendix A for a description of corresponding foods

EXAMPLE 3

Low-Fat Diet (20% of Total Calories Are Fat Calories)

Primary Criteria
APO E4 genotype (highest risk)
Secondary Criteria
a) Triglycerides ≧1000 (mg/dL)
b) LDL-C ≧160 (mg/dL)
Recommended Diet Plan

| Food | 1200 cals. | 1600 cals. | 1800 cals. | 2000 cals. | 2400 cals. | 2800 cals. | 3000 cals. | 3600 cals. |
|---|---|---|---|---|---|---|---|---|
| Grain/Starch | 5 | 7 | 8 | 9 | 11 | 13 | 14 | 17 |
| Vegetable | 6 | 6 | 6 | 9 | 11 | 11 | 12 | 13 |
| Fruit | 1 | 2 | 3 | 3 | 4 | 4 | 4 | 6 |
| Dairy | 2 | 3 | 3 | 3 | 3 | 4 | 4 | 4 |
| Protein | 6 | 8 | 9 | 10 | 11 | 13 | 14 | 17 |
| Fat | 3 | 4 | 5 | 5 | 6 | 7 | 7 | 9 |
| Sweets/Alcohol | 0 | 0 | 0 | 0 | 0 | 0 | 0 | 0 |

Figure 3:
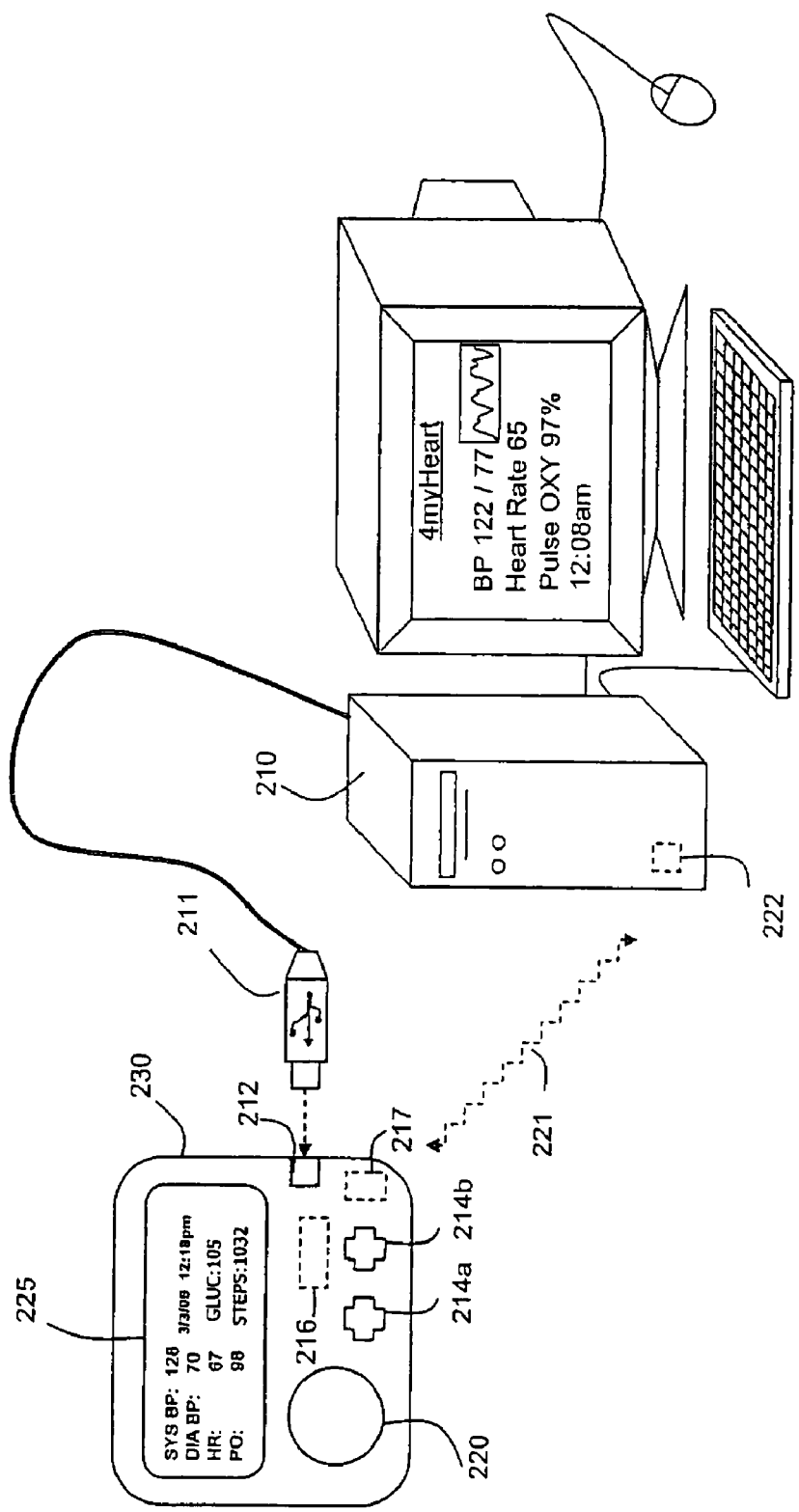
FIG. 3 is a semi-schematic view of the monitoring device from FIG. 1 that connects through a USB port to a personal computer; and, FIG. 4 shows a report generated from the health management system of FIG. 1 that displays results from a patient's Apo E blood test.

Note
values in columns refer to points, see Appendix A for a description of corresponding foods Referring to FIG. 3, the above-described monitoring device 230 that provides vital sign and exercise information to the algorithm includes a USB port 212 through which it uploads and downloads information from an Internet-accessible personal computer 210. The personal computer 210, in turn, connects to the Internet-based software system. The USB port 212 typically connects to the personal computer 210 through a first cable 211. The monitoring device 230, which during use is typically attached to the patient's belt, features: i) an integrated, optical 'pad sensor' 220 that cufflessly measures blood pressure, pulse oximetry, and heart rate from a patient's finger as described in more detail below; and ii) an integrated pedometer circuit 216 that measures steps and, using an algorithm, calories burned. To receive information from external devices, the monitoring device 230 also includes a short-range wireless transceiver 217 that receives information such as body weight and percentage of body fat from an external scale. The wireless transceiver 217 can also receive information from another external device, such as a glucometer that includes a matched wireless transceiver. The wireless transceiver 217 can also connect through a wireless link 221 to the personal computer 210, which in this case includes a matched transceiver 222. The patient views information stored in the monitor using an LCD 225, and can interact with the monitor 230 (e.g., reset or reprogram it) using a series of buttons 214a, 214b.

Methods used by the monitoring device for measuring vital signs and particularly cuffless blood pressure are described in the following co-pending patent applications, the entire contents of which are incorporated by reference: 1) CUFFLESS BLOOD-PRESSURE MONITOR AND ACCOMPANYING WIRELESS, INTERNET-BASED SYSTEM (U.S. Ser. No. 10/709,015; filed Apr. 7, 2004); 2) CUFFLESS SYSTEM FOR MEASURING BLOOD PRESSURE (U.S. Ser. No. 10/709,014; filed Apr. 7, 2004); 3)CUFFLESS BLOOD PRESSURE MONITOR AND ACCOMPANYING WEB SERVICES INTERFACE (U.S. Ser. No. 10/810,237; filed Mar. 26, 2004); 4) BLOOD PRESSURE MONITORING MONITOR FEATURING A CALIBRATION-BASED ANALYSIS (U.S. Ser. No. 10/967,610; filed Oct. 18, 2004); 5) PERSONAL COMPUTER-BASED VITAL SIGN MONITOR (U.S. Ser. No. 10/906,342; filed Feb. 15, 2005); 6) PATCH SENSOR FOR MEASURING BLOOD PRESSURE WITHOUT A CUFF (U.S. Ser. No. 10/906,315; filed Feb. 14, 2005); and 7) SMALL-SCALE, VITAL SIGNS MONITORING MONITOR, SYSTEM AND METHOD (U.S. Ser. No. 10/907440; filed Mar. 31, 2005).

FIG. 4 shows a web-based report 240 rendered by the Internet-based system that features a first region 245 describing LDL cholesterol sub-classes and Apo E, and a second region 246 that describes blood test information taken from a series of conventional blood tests. The report 240 also includes a link 247 that, when clicked, renders a personalized diet plan based on the patient's Apo E genotype and personal information. The web page is typically made available to both the patient and a medical professional through separate interfaces. Parameters in the first 245 and second 246 regions are compared to values recommended by the medical professional associated with the Internet-based system. Typically, these parameters are color-coded according to how they compare to the recommended values, and are grouped into the following categories: 'below goal' 241; 'above goal, below alert' 242; and 'above alert' 243. 'below goal' 241 means a parameter has not met the goal established by the medical professional. Parameters that meet a goal, but fall under the status of an 'alert', are categorized as 'above goal, below alert' 242. A parameter that increases beyond that set by the medical professional falls into 'above alert' status 243. The web page also includes a link 249 that renders a PDF document describing the report's results, and a link 250 for printing the report.

Other embodiments are also within the scope of the invention. In particular, after processing the Apo E information, the algorithm can recommend diets other than those described in the above-mentioned examples. These diets can be structured in a number of different ways, such as number of calories, 'points' corresponding to certain food groups, number of carbohydrates, types of foods, etc.

In other embodiments, the web pages used to display information described above can take many different forms, as can the manner in which the data are displayed. Web pages are typically written in a computer language such as 'HTML' (hypertext mark-up language), and may also contain computer code written in languages such as Java and Java script for performing certain functions (e.g., sorting of names). The web pages are also associated with database software (provided by companies such as Oracle and Microsoft) that is used to store and access data. Equivalent versions of these computer languages and software can also be used. In general, the graphical content and functionality of the web pages may vary substantially from what is shown in the above-described figures. In addition, web pages may also be formatted using standard wireless access protocols (WAP) so that they can be accessed using wireless devices such as cellular telephones, personal digital assistants, and related devices.

Different web pages may be designed and accessed depending on the end-user. As described above, individual users have access to web pages that only their vital sign information (i.e., the patient interface), while organizations that support a large number of patients (e.g. hospitals) have access to web pages that contain information from a group of patients (i.e., the physician interface). Other interfaces can also be used with the web site, such as interfaces used for: hospitals, insurance companies, members of a particular company, clinical trials for pharmaceutical companies, and e-commerce purposes. Vital sign information displayed on these web pages, for example, can be sorted and analyzed depending on the patient's medical history, age, sex, medical condition, and geographic location.

The web pages also support a wide range of algorithms that can be used to analyze data once it is extracted from the data packets. For example, the above-mentioned text message or email can be sent out as an 'alert' in response to vital sign or blood test information indicating a medical condition that requires immediate attention. Alternatively, the message could be sent out when a parameter (e.g. blood pressure, heart rate) exceeded a predetermined value. In some cases, multiple parameters can be analyzed simultaneously to generate an alert message. In general, an alert message can be sent out after analyzing one or more data parameters using any type of algorithm. These algorithms range from the relatively simple (e.g., comparing blood pressure to a recommended value) to the complex (e.g., predictive medical diagnoses using 'data mining' techniques). In some cases data may be 'fit' using algorithms such as a linear or non-linear least-squares fitting algorithm. In general, any algorithm that processes data collected with the above-described method is within the scope of the invention.

In certain embodiments, the above-described information can be used to characterize a wide range of maladies, such as diabetes, metabolic syndrome, heart disease, congestive heart failure, sleep apnea and other sleep disorders, asthma, heart attack and other cardiac conditions, stroke, Alzheimer's disease, obesity, and hypertension.

APPENDIX A

Food as Points: healthy, not-as-healthy, and splurge
Cardioprotective floods (soluble fiber, omega-3 & mono-unsaturated fatty acids, soy protein, calcium, and plant sterols) lower cholesterol and other markers of cardiovascular risk.

| HEALTHY | NOT AS HEALTHY | SPLUGE | |
|---|---|---|---|
| Grain/Starch (1 point = serving, size varies, see below) | | | |
| 1 slice pumpernickel, oat bran, rye bread | 1 slice enriched white bread or wheat bread | 1 buscuit small muffin | POINTS |
| ¼ whole grain bagel | ½ English muffin | 1 peice cornbread | |
| ½ whole grain bagel | ½ white bun | 9 snack chips | |
| ½ whole wheat pita | 2 rice cakes | 6 in taco shell | |
| 5 in corn tortilla | 15 snack chips (fat Free, baked) | ¾ c sugared dry cereals | |
| 6 in whole wheat tortilla | 6 in flour tortilla | ¼ c commercial granola | |
| ½ c high (>4 gms) fiber, dry cereal (BranBuds, All Bran, FiberOne, Kashi) | 1½ c puffed cereals (puffed wheat, Rice Krispies) | 24 oyster crackers 6 butter type crackers (Ritz) | |
| ¼ c lowfat granola, muesli | ¼ c Grapenuts | 2-5 (¾ oz) wheat crackers (fat added) | |
| ½ c cooked cerals (oatmeal, oat bran, barley, Wheatina) | 13 c grits or hominy ⅓ c couscous | (Triscuit, Wheat Thins) 6 saltine crackers | |
| ½ c bulgar | 5 wheat crackers (no fat added) | 1 c croutons | |
| 2 rye crispbreads (RyVita, Kavti, Wasa) | ⅓ c of white pasta | ½ c mashed potato | |
| ⅓ c of whole wheat pasta | ⅓ c of white rice | 1 c french fries (oven baked) | |
| ⅓ c of brown rice | ¾ oz pretzels | 4 in pancake | |
| ¾ oz whole wheat pretzels | ⅔ (3 oz) terge baked potato (with skin) | ½ sweet roll/plain donut | |
| ⅓ c sweet potato, yam, pumpkin | | | |
| 1/7 c corn or green peas | waffle (A in square) | | |
| 3 c popcorn (no oil) | | | |
| Vegetable (1 point = ½ cooked, 1 c raw) | | | |
| artichoke | bean sprouts | high sodium tomato juice | POINTS |
| 6 spears asparagus | watercress | pickles | |
| green beans | celery | sauerkraut | |
| broccoli | cucumber | | |
| brussels sprouts | pea pods | | |
| carrots | water chestnuts | | |
| cauilfiower | radishes | | |
| eggplant | tomato sauce | | |
| greens (kale, collard, turnip, chard, okra) | zucchini | | |
| squash | mushrooms | | |
| tomatoes (fresh or canned with skin) | salad greens | | |
| turnips, parsnips, beets | | | |
| onions, leeks, scallions | | | |
| spinach | | | |
| cabbage | | | |
| peppers | | | |
| garlic | | | |
| Fruit (1 point = 1 medium piece, ½ c canned/chopped fruit, ¼ c dried, ½ c juice) | | | |
| ¾ c berries (strawberries, blackberries) | applesauce | 100% fruit juice / commercial fruft juice | POINTS |
| 1 orange / 2 tangerines | ¾ c Mandarin oranges | ½ grapefruit (if on Statin medicine) | |
| 4 fresh apricots / 7 halves dried | canned Fruit | | |
| 1 plum | fruit cocktail | | |
| 1 nectarine / 1 peach | | | |
| ½ tropical fruit (banana, mango, papaya) | | | |
| 1 fresh apple / 4 rings dried | | | |
| ½ pear | | | |
| 1½ figs (dried) | | | |
| 3 medium prunes | | | |
| 1¼ c melon Cantaloupe, watermelon) | | | |
| 12 cherries / 15 grapes | | | |
| 2 T dried cranberries/raisins | | | |
| Dairy (1 point = serving size varies, see below) | | | |
| 1 c nonfat or ½% or 1% milk | 1 c 2% milk | 1 c whole milk (plain or flavored) | POINTS |
| ⅔ c non fat plain yogurt | ⅔ c lowfat plain yogurt | ⅔ c regular yogurt | |
| 1 c soymilk | 1 c buttermilk | 1 c goat milk | |
| ½ c evaporated nonfat milk | ⅔ c flavored nonfat yogurt | ½ c evaporated milk | |
| ⅓ c dry nonfat milk | | 1 c kefir | |
| ⅔ c soy plain yogurt | | ⅔ c lowfat flavored yogurt | |

APPENDIX A-continued

Food as Points: healthy, not-as-healthy, and splurge
Cardioprotective floods (soluble fiber, omega-3 & mono-unsaturated fatty acids, soy protein, calcium, and plant sterols) lower cholesterol and other markers of cardiovascular risk.

| HEALTHY | NOT AS HEALTHY | SPLUGE | |
|---|---|---|---|

Protein (1 point = 1 oz, 1 oz cooked meat without fat unless otherwise as stated)

| | | | |
|---|---|---|---|
| ANIMAL SOURCES<br>nonfat cheese (<3 g fat);<br>¼ c nonfat/lowfat cottage cheese<br>poultry: white meat, no skin<br>(turkey, chicken, Cornish hen)<br>wild game: no skin<br>fresh & salt water fish<br>(salmon, bluefish, swordfish, trout)<br>canned fish in water (mackerel, herring, tuna, sardines, salmon)<br>shellfish (crab, lobster, shrimp, 6 oysters)<br>lunch meat (<3 g fat)<br>¼ c egg substitute or 2 egg whites<br><br>PLANT SOURCES<br>soy cheese<br>½ c beans or legumes<br>(kidney, pinto, garbanzo, lentil, peas)<br>⅓ c lima beans<br>¼ c soy beans<br>½ soy burger<br>1½ oz firm (raw) tofu<br>4 oz (or ½ c) regular tofu<br>¼ c tempeh | ANIMAL SOURCES<br>lowfat cheese (3-5 g fat); feta,<br>Mozzarella, 2 T cantaloupe or<br>lowfat Ricotta<br>¼ c cottage cheese<br>poultry: dark meat, no skin<br>lamb (roast, chop, leg)<br>lean beef (round, sirloin, flank, roast)<br>fries fish (no batter)<br>lowfat hot dog (turkey or chicken)<br>pork (ham, loin, chop, cutlet)<br>lunch meat (3-5 g fat)<br>Canadian bacon<br>1 egg<br><br>PLANT SOURCES<br>½ slice vegetarian lunch meat<br>1 soy-based hot dog<br>1 soy-based sausage | ANIMAL SOURCES<br>regular cheese (8 g fat):<br>cheddar, American<br>poultry: dark meat, with skin<br>sausage (bratwurst, Italian, knockwurst)<br>fried and battered fish<br>hot dog (beef, pork or combo)<br>pork ribs, ground pork, pork sausage<br>lunch meat (8 g fat)<br>3 slices of bacon | POINTS |

Fat (1 point = serving size varies, see below)

| | | | |
|---|---|---|---|
| 2 t plant sterol enriched spread (Benecol)<br>1 T light plant spread (Benecol Light)<br>4 T or 1 oz avocado<br>1 t canola, olive, flax seed oil<br>8 black or 10 green stuffed olives<br>6 almonds, cashews<br>10 peanuts<br>4 pecans or walnuts<br>3 T ground flax seeds<br>2 t nut butter (peanut, almod, sesame)<br>1 T sesame, pumpkin, sunflower seeds | 1 t non-hydrogenated (non-hy)<br>margarine<br>1 T lowfat non-hy margarine<br>1 t mayonnaise or 1 t tartar sauce<br>1 T non-hy light mayonnaise<br>1 t corn, safflower, soybean oil<br>1 T salad dressing<br>2 T reduced fat non-hy salad dressing<br>3 T reduced fat non-hy sour cream<br>1 T fat free cream cheese | 1 t butter<br>1 t hydrogenated<br>margarine<br>2 t whipped butter<br>1 T reduced fat butter<br>1 T coconut milk<br>1 T cream cheese<br>2 T reduced fat cream cheese<br>2 T Half & Half<br>2 T sour cream<br>2 T coconut (sweetened, shredded)<br>1 t shortening or lard<br>2 T gravy (meat) | POINTS |

Sweet and Alcohol (1 point = serving size varies, see below)

| | | | |
|---|---|---|---|
| 1 T cocoa powder (unsweetened)<br>3 oz fruit juice bar<br>⅓ c nonfat frozen yogurt<br>1 T 100% fruit spread<br>½ c sugar free pudding/gelatin<br>sugar substitutes (serving on package)<br>½ c fat free ice cream or sorbet<br>3 gingersnaps, graham crakers<br>1 piece angel food cake | 2 T chocolate syrup<br>½ c frozen yogurt<br>1 T jam<br>1 T honey, brown or white sugar<br>½ c lowfat ice cream<br>2 T light maple syrup | 1½ oz hard alcohol<br>4 oz wine<br>12 oz of beer<br>1 T jelly<br>1 T maple syrup<br>½ c ice cream<br>12 oz soda/sweet tea<br>1 chocolate kisses | POINTS |

UNITS

T = tablespoon t = teaspoon c = cup oz = ounces in = inch g = gram

ABBREVIATION non-hy = non-hydrogenated

Still other embodiments are within the scope of the following claims.

We claim:

1. A method for selecting a diet plan for a patient, comprising
   (a) determining the Apo E genotype of the patient; and
   (b) selecting a diet plan based on the Apo E genotype of the patient;
   wherein the diet plan comprises:
      (i) a moderate-fat diet (35% fat) when the patient's Apo E genotype is e2/2 or e2/3;
      (ii) a preventative (25% fat) diet when the patient's Apo E genotype is e3/3 or e2/4; or
      (iii) a low-fat (20% fat) diet when the patient's Apo E genotype is e4/4 or e3/4.

2. A method for preventing cardiovascular disease in a patient with an increased risk of developing cardiovascular disease comprising:
   (a) determining the Apo E genotype of the patient;
   (b) prescribing a low-fat diet (20% fat) to the patient when the Apo E genotype of the patient determined from (a) is e4/4 or e3/4.

3. A method for preventing cardiovascular disease in a patient with an increased risk of developing cardiovascular disease comprising:
   (a) determining the Apo E genotype of the patient;
   (b) identifying the patient as having an increased risk of developing cardiovascular disease when the Apo E genotype of the patient determined from (a) is e4/4 or e3/4;
   (c) prescribing a low-fat diet (20% fat) to the patient.

4. A method for preventing cardiovascular disease in a patient with an increased risk of developing cardiovascular disease comprising:
   (a) determining the Apo E genotype of the patient;
   (b) identifying the patient as having an increased risk of developing cardiovascular disease when the Apo E genotype of the patient determined from (a) is e4/4 or e3/4;
   (c) selecting a low-fat diet (20% fat) for the patient identified in (b); and
   (d) prescribing the diet selected in step (c) to the patient.

* * * * *